United States Patent [19]

Partika et al.

[11] Patent Number: 5,781,007
[45] Date of Patent: Jul. 14, 1998

[54] PORTABLE THREE AXIS SCANNER TO INSPECT A GAS TURBINE ENGINE SPOOL BY EDDY CURRENT OR ULTRASONIC INSPECTION

[75] Inventors: Mark Partika, Middletown; Michael L. Dziech, Cincinnati; Jon R. Dierdorf, Okeana, all of Ohio; Scott A. Whitlow, Salem, Oreg.; Fred L. Perrin, Jr., Kennewick; Richard W. Smith, Richland, both of Wash.

[73] Assignee: General Electric Company, Cincinnati, Ohio

[21] Appl. No.: 735,940

[22] Filed: Oct. 23, 1996

Related U.S. Application Data

[60] Provisional application No. 60/007,006 Oct. 24, 1995.
[51] Int. Cl.$^6$ ............................. G01N 27/90; G01H 11/02
[52] U.S. Cl. .................. 324/220; 324/227; 324/262; 324/261; 73/660
[58] Field of Search .................... 324/220, 262, 324/234, 236–243, 260, 261; 73/660, 661

[56] References Cited

U.S. PATENT DOCUMENTS 4,468,620  8/1984  Vaerman ........................ 324/261
4,644,274  2/1987  Casarcia ........................ 324/226
5,315,234  5/1994  Sutton, Jr. et al. ............. 324/242
5,442,285  8/1995  Zombo et al. ................... 324/227
5,670,897  9/1997  Zombo et al. ................... 324/227

Primary Examiner—Sandra L. O'Shea
Assistant Examiner—Jay M. Patidar
Attorney, Agent, or Firm—Andrew C. Hess; Nathan D. Herkamp

[57] ABSTRACT

A portable three axis scanner is usable to inspect a gas turbine engine spool in situ upon removing a fan module from the engine. The scanner includes a drive assembly mountable to a forward end of the spool, and a support assembly mountable to an aft end of the spool. A support beam extends between the drive and support assemblies, and a carriage assembly is mounted thereon. The carriage assembly includes a probe support for mounting a removable scanner probe for inspecting the inside of the spool by ultrasonic or eddy current inspection. The drive assembly includes means for axially translating the carriage assembly, means for rotating the carriage assembly, and means for radially translating the probe support and probe thereon so that the probe has three-axis movement including axial, circumferential, and radial, respectively, for being selectively positioned inside the spool between the forward and aft ends thereof for inspecting the spool.

20 Claims, 11 Drawing Sheets

PORTABLE THREE AXIS SCANNER TO INSPECT A GAS TURBINE ENGINE SPOOL BY EDDY CURRENT OR ULTRASONIC INSPECTION

CROSS REFERENCE TO RELATED APPLICATIONS

This application claims the benefit of U.S. Provisional Application No. 60/007,006, filed Oct. 24, 1995.

The present invention relates generally to maintenance inspection of a gas turbine engine, and, more specifically, to ultrasonic and eddy current inspection in situ in a gas turbine engine.

BACKGROUND OF THE INVENTION

One type of aircraft gas turbine engine is manufactured and assembled in discrete modules. A fan module is joined in turn to a compressor module, a high pressure turbine (HPT) module, and a low pressure turbine (LPT) module. The fan module includes a plurality of fan blades driven by a drive shaft for powering the aircraft in flight. The compressor module includes several rows of compressor rotor blades extending radially outwardly from a common spool within an outer stator casing which supports corresponding rows of stator vanes. The HPT module includes an annular combustor and the several stages of the turbine, with their corresponding rotor blades and nozzle vanes supported by a portion of the outer casing. The HPT module may also include at its forward end additional stages of the compressor if desired. And, the LPT module typically includes several stages of rotor blades and their corresponding stator vanes supported by another portion of the outer casing. The center of the gas turbine engine is hollow and includes respective drive shafts for powering the fan module by the LPT module, and powering the compressor module by the HPT module.

During a typical maintenance outage of the engine, its various components are inspected, and in particular the various rotor components. Two types of conventional inspection for uncovering surface or subsurface defects such as cracks, voids or inclusions, are ultrasonic testing and eddy current testing. In ultrasonic testing, a transducer emits ultrasonic waves through a coupling fluid such as water into the inspection component for detecting any defects to a predetermined depth below the surface. In eddy current testing, a helical coil generates an AC magnetic field directed at the surface of the components for detecting defects at the surface thereof.

However, in order to inspect internal engine components such as the compressor spool, the compressor module must be separated from its adjacent modules and completely disassembled removing the outer casing and stationary components, as well as reducing the several stages of rotor blades to provide access to the spool. The rotor spool includes a plurality of adjoining disks each having an inner bore, side surfaces, and chamfers therebetween. To inspect these regions, the forward and aft portions of the spool assembly must also be removed to provide adequate internal access thereto. The entire disassembled rotor spool is then immersed in a tank containing water, and then conventional ultrasonic and eddy current inspection probes are separately utilized for performing the respective inspection of the bores, faces, and chamfers. This is a complex, prolonged, and expensive method for inspecting the compressor rotor spool.

SUMMARY OF THE INVENTION

A portable three axis scanner is usable to inspect a gas turbine engine spool in situ upon removing a fan module from the engine. The scanner includes a drive assembly mountable to a forward end of the spool, and a support assembly mountable to an aft end of the spool. A support beam extends between the drive and support assemblies, and a carriage assembly is mounted thereon. The carriage assembly includes a probe support for mounting a removable scanner probe for inspecting the inside of the spool by ultrasonic or eddy current inspection. The drive assembly includes means for axially translating the carriage assembly, means for rotating the carriage assembly, and means for radially translating the probe support and probe thereon so that the probe has three-axis movement including axial, circumferential, and radial, respectively, for being selectively positioned inside the spool between the forward and aft ends thereof for inspecting the spool.

BRIEF DESCRIPTION OF THE DRAWINGS

The invention, in accordance with preferred and exemplary embodiments, together with further objects and advantages thereof, is more particularly described in the following detailed description taken in conjunction with the accompanying drawings in which.

DESCRIPTION OF THE PREFERRED EMBODIMENT(S)

Figure 1:
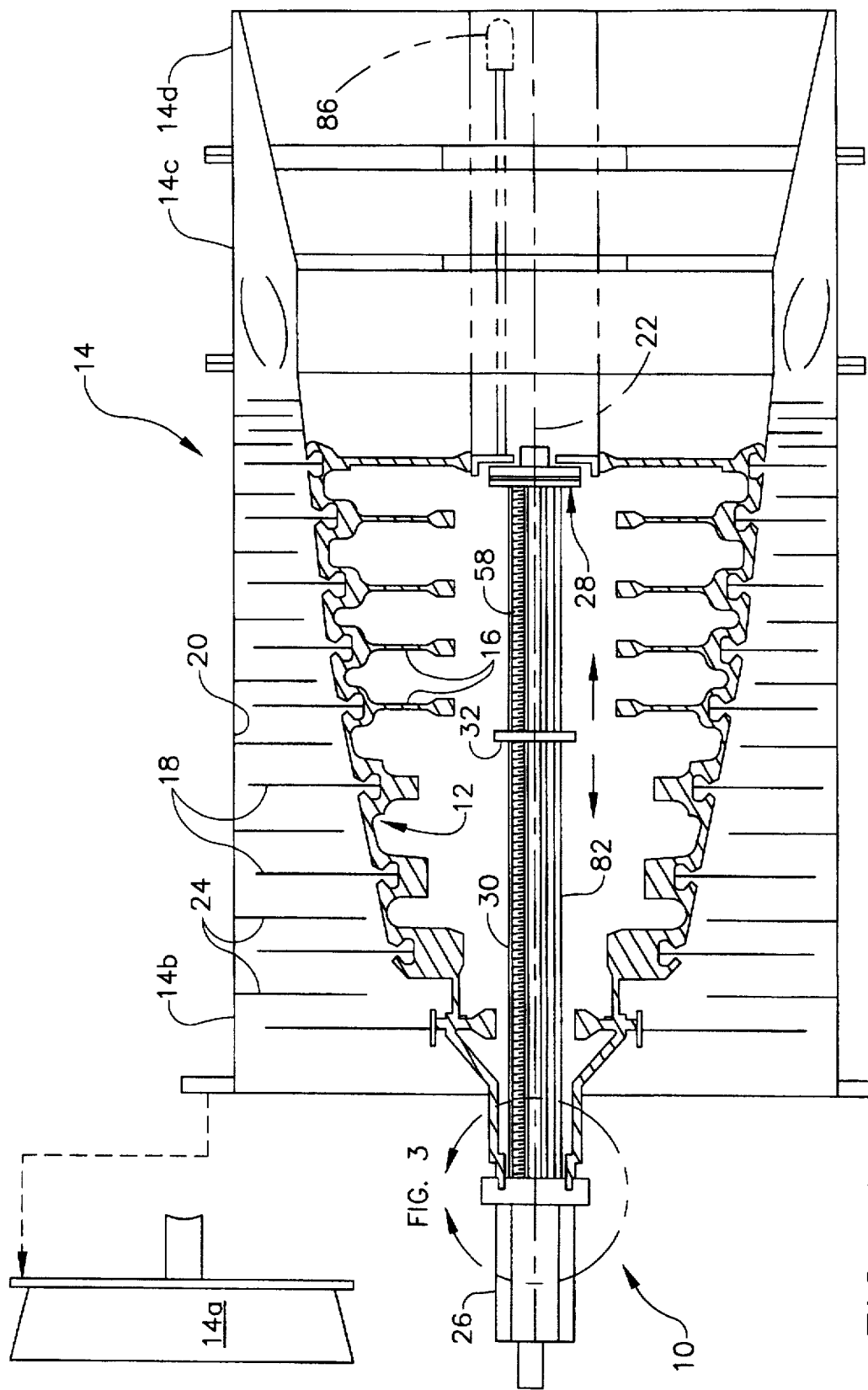
FIG. 1 is a schematic axial representation of an aircraft gas turbine engine having a portable three axis scanner mounted to a compressor spool thereof.

Illustrated schematically in FIG. 1 is a portable three axis scanner 10 according to one embodiment of the present invention for inspecting the inside of a gas turbine engine compressor rotor spool 12. An exemplary conventional aircraft gas turbine engine 14 is illustrated schematically and includes four separate modules which may be assembled together to complete the engine 14. A conventional fan module 14a is suitably joined in turn to a compressor module 14b, a high pressure turbine (HPT) module 14c, and a low pressure turbine (LPT) module 14d at suitable flanges, all of which modules are conventionally configured as assemblies of components.

The fan module 14a conventionally includes fan rotor blades extending from a fan disk and driven by the HPT module 14c by a drive shaft. The compressor module 14b includes the compressor rotor spool 12 which is an integral assembly of suitably configured axially spaced apart rotor disks 16 for compressor stages two though ten of the engine. Extending radially outwardly from the rotor disks 16 are respective compressor rotor blades 18.

The engine 14 includes an annular outer casing 20 disposed coaxially with the compressor rotor spool 12 about an axial or longitudinal centerline axis 22 of the engine. Supported by the outer casing 20 and extending radially inwardly therefrom are corresponding rows of compressor stator vanes 24 which are positioned between respective rows of the rotor blades 18.

The HPT module 14c includes a conventional combustor therein and one or more stages of high pressure turbine rotor blades extending outwardly from respective rotor disks, with a respective plurality of turbine nozzle vanes extending radially inwardly from a portion of the outer casing 20. In this exemplary embodiment, the HPT module 14c also includes several aft stages, i.e. stage eleven et seq. of the compressor.

The LPT module 14d similarly includes several stages of rotor blades extending outwardly from respective rotor disks, with a plurality of corresponding nozzle vanes extending radially inwardly from another portion of the outer casing 20.

When completely assembled, the four modules 14a–d are coaxially aligned about the centerline axis 22, with the LPT module 14d driving the fan module 14a through one drive shaft, and the HPT module 14c driving the compressor module 14d through another coaxial drive shaft in a conventionally known manner.

During a maintenance outage of the engine 14, it is desirable to inspect the various components thereof including the several rotor disks 16 of the compressor rotor spool 12. In the prior art, this would require complete disassembly of the compressor module 14b itself with the removal of the outer casing 20, the stator vanes 24, and rotor blades 18. The compressor module 14b must also be separated from the fan module 14a and the HPT module 14c to provide access to both ends thereof, with the stage two and the stage ten disks being typically additionally removed to provide adequate access to the inside of the spool 12. The entire spool 12 would then be immersed in a water tank for undergoing conventional ultrasonic and eddy current inspection.

However, in accordance with the present invention, the compressor spool 12 may be inspected in situ maintaining substantially complete assembly of the compressor module 14b by simply removing the fan module 14a from the assembled gas turbine engine 14 for providing access to the forward end of the compressor spool 12. The HPT module 14c and the LPT module 14d may also be removed from the compressor module 14b if desired, although it is not necessary to do so in practicing the present method of inspection.

Figure 2:
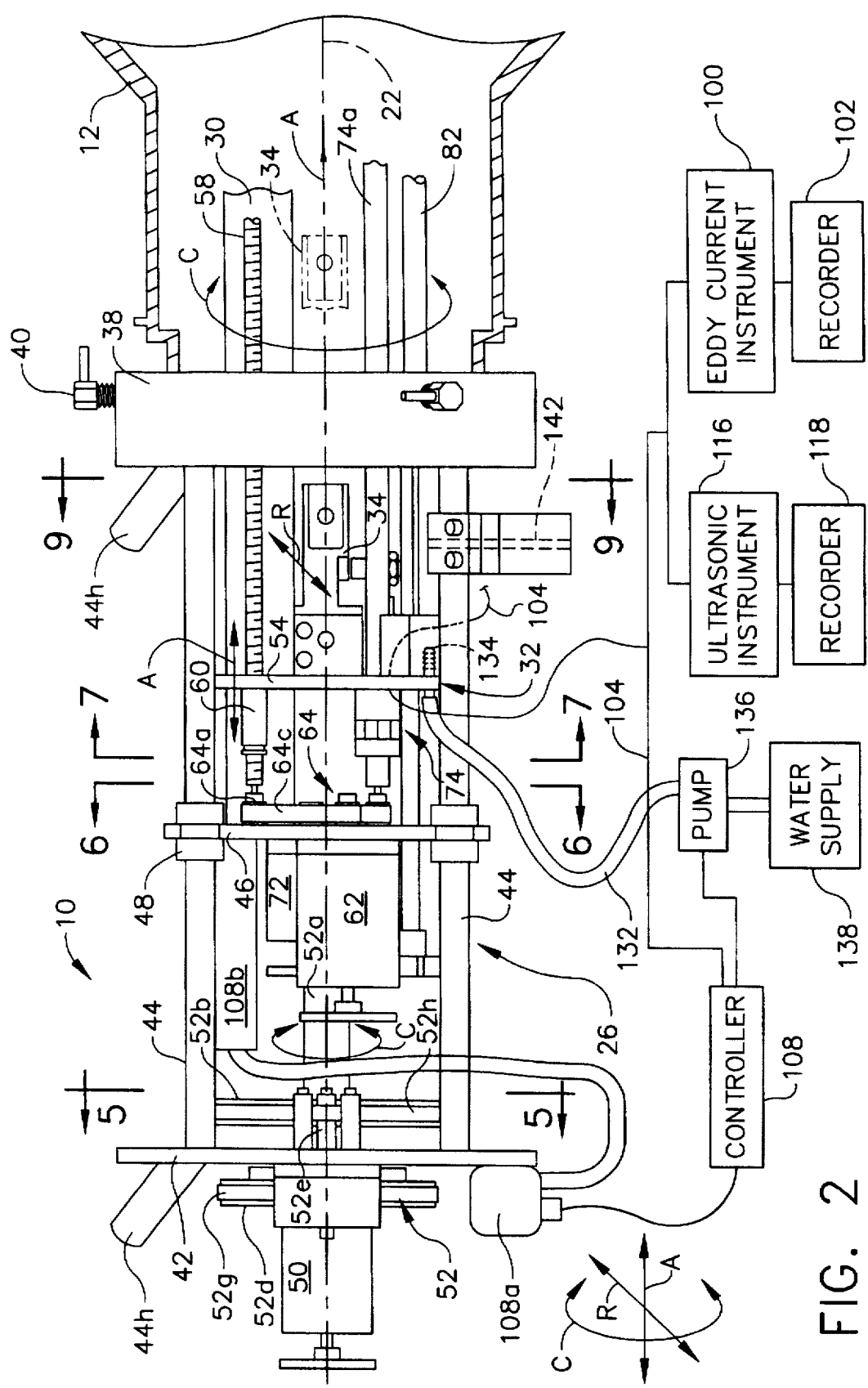
FIG. 2 is a partly schematic side view of the scanner illustrated in FIG. 1 including a drive assembly and carriage assembly thereof mounted to the forward end of the compressor spool.

Upon removing the fan module 14a, the portable scanner 10 may be readily mounted to the compressor spool 12 for conducting ultrasonic and eddy current inspection of the rotor disk 16 thereof. As shown in FIG. 1, the scanner 10 is an assembly of components which is removably fixedly mountable to the forward and aft ends of the spool 12. The scanner 10 includes at its froward end a drive assembly 26 removably fixedly mountable to the forward end of the spool 12. The scanner 10 also includes at its aft end an aft support assembly 28 which is also removably fixedly mountable to the aft end of the spool 12. A single support beam 30 extends between the drive and support assemblies 26, 28. And, a carriage assembly 32 is mounted on the support beam 30 and is selectively movable axially between the drive and support assemblies 26, 28 for inspecting the rotor disk 16. As shown in FIG. 2, the carriage assembly 32 includes a probe support 34 from which extends a removable scanner probe as described below for inspecting the inside of the spool 12.

Figure 4:
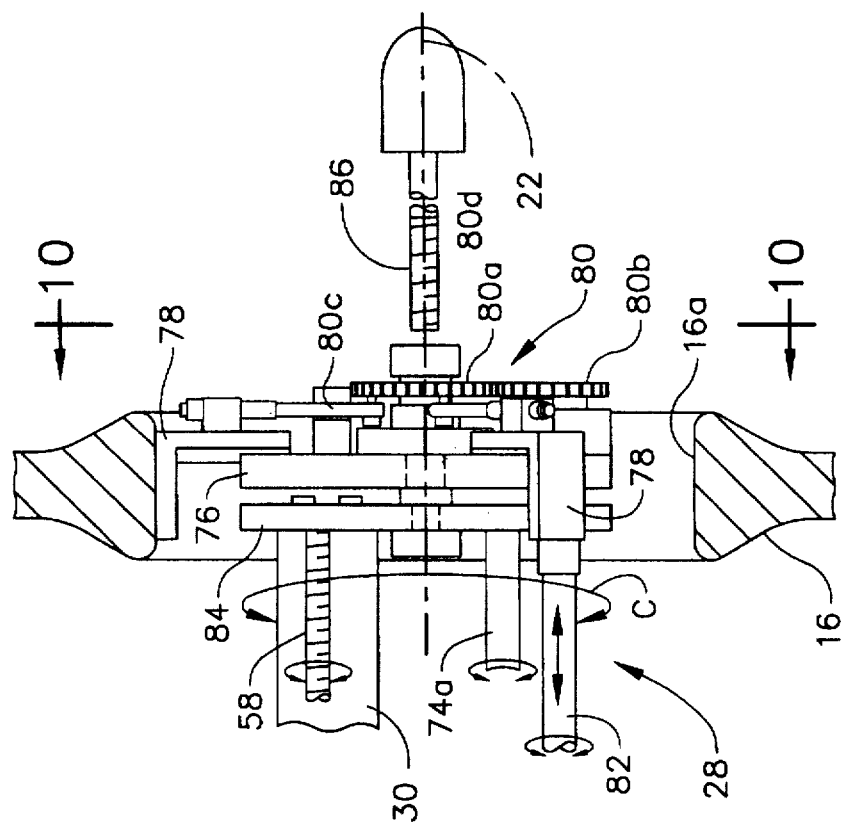
FIG. 4 is a side view of an aft support assembly of the scanner illustrated in FIG. 1 joined to the aft end of the compressor spool.
Figure 3:
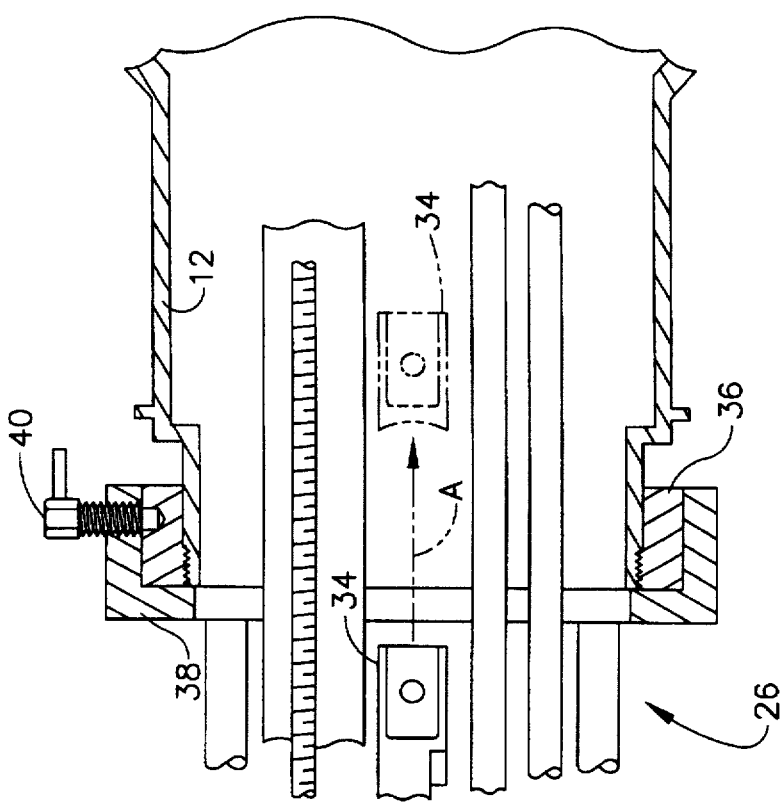
FIG. 3 is an enlarged, axial sectional view of the forward end of the compressor spool shown within the circle labeled 3 in FIG. 1 showing the drive assembly mounted on an adaptor collar joined to the forward end of the compressor spool.

The scanner 10 is illustrated in more particularity in FIGS. 2–4. Referring firstly to FIG. 3, the forward end of the compressor spool 12 is threaded for receiving the fan module in a conventionally known manner. Upon removal of the fan module 14a, the threads are made available for mounting the drive assembly 26 thereto. A threaded annular collar 36 is initially mounted on the threads of the forward end of the spool 12. The aft end of the drive assembly 26 includes a tubular or annular mounting flange 38 which is rabbetted to closely fit around the collar 36. Three equally spaced apart radial retention pins 40 are preferably spring loaded to slide radially through the mounting flange 38 into respective apertures in the collar 36 for rigidly securing the drive assembly 26 to the forward end of the compressor spool 12. In this way, the drive assembly 26 is maintained stationary with the compressor spool 12.

Referring to FIG. 2, the drive assembly 26 includes suitable means for selectively axially translating the carriage assembly 32 along the longitudinal axis 22; suitable means for selectively rotating the carriage assembly 32 about the longitudinal axis 22; and suitable means for radially translating the probe support 34 on the carriage assembly 32 so that the probe support 34 has three-axis movement including axial (A) circumferential (C), and radial (R), respectively, for being selectively positioned inside the spool 12 between the forward and aft ends thereof for inspecting the disks 16 inside the spool 12.

Referring again to FIG. 2, the drive assembly 26 further includes a base plate 42 spaced axially forwardly from the mounting flange 38, and a plurality of circumferentially spaced apart frame rods 44 extend axially between the base plate 42 and the mounting flange 38 and are suitably fixedly joined thereto. Suitable handles 44h are provided at both ends of the drive assembly 26 so that it may be readily handled and placed into position on the collar 36.

Figure 5:
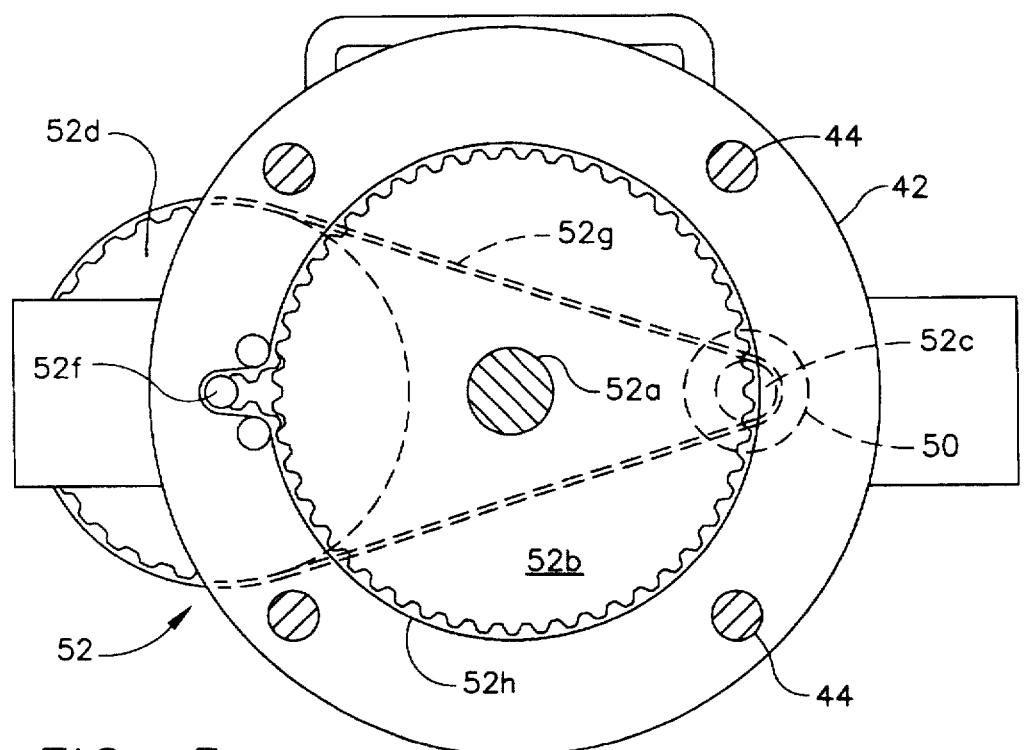
FIG. 5 is a partly sectional, elevational, aft-facing-forward view of circumferential rotation drive means at the forward end of the drive assembly illustrated in FIG. 2 and taken along line 5—5.
Figure 6:
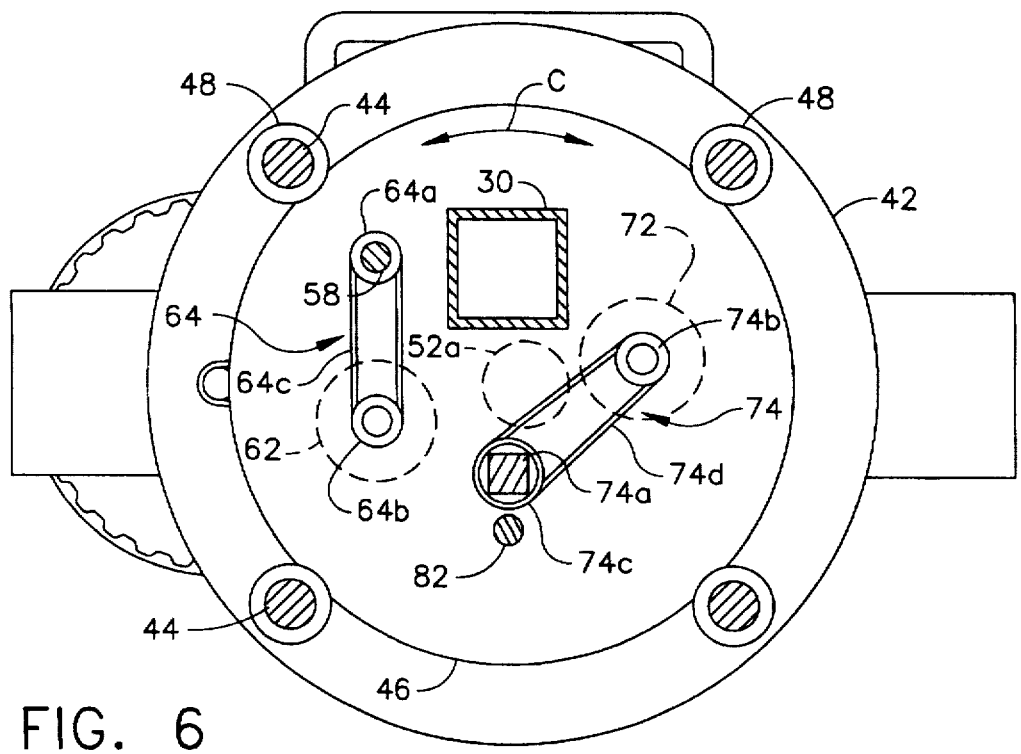
FIG. 6 is a partly sectional, elevational, aft-facing-forward view of a circumferential drive plate disposed at an intermediate position in the drive assembly illustrated in FIG. 2 and taken along line 6—6.

An annular, circumferential-drive (CD) plate 46 as shown in FIGS. 2 and 6 is mounted to the frame rods 44 by suitable grooved bushings 48 for circumferential rotation (C) within or between the rods 44 about the centerline axis 22. The carriage assembly 32 and the support beam 30 are joined to the CD plate 46 for circumferential rotation (C) therewith. A circumferential-drive (CD) motor 50 is fixedly joined to the base plate 42, and has an optional hand wheel for manually rotating its output shaft. As shown in FIGS. 2 and 5, a circumferential-drive (CD) transmission 52 is joined between the CD motor 50 and the CD plate 46 for rotating the CD plate 46 circumferentially about the longitudinal axis 22.

Figure 7:
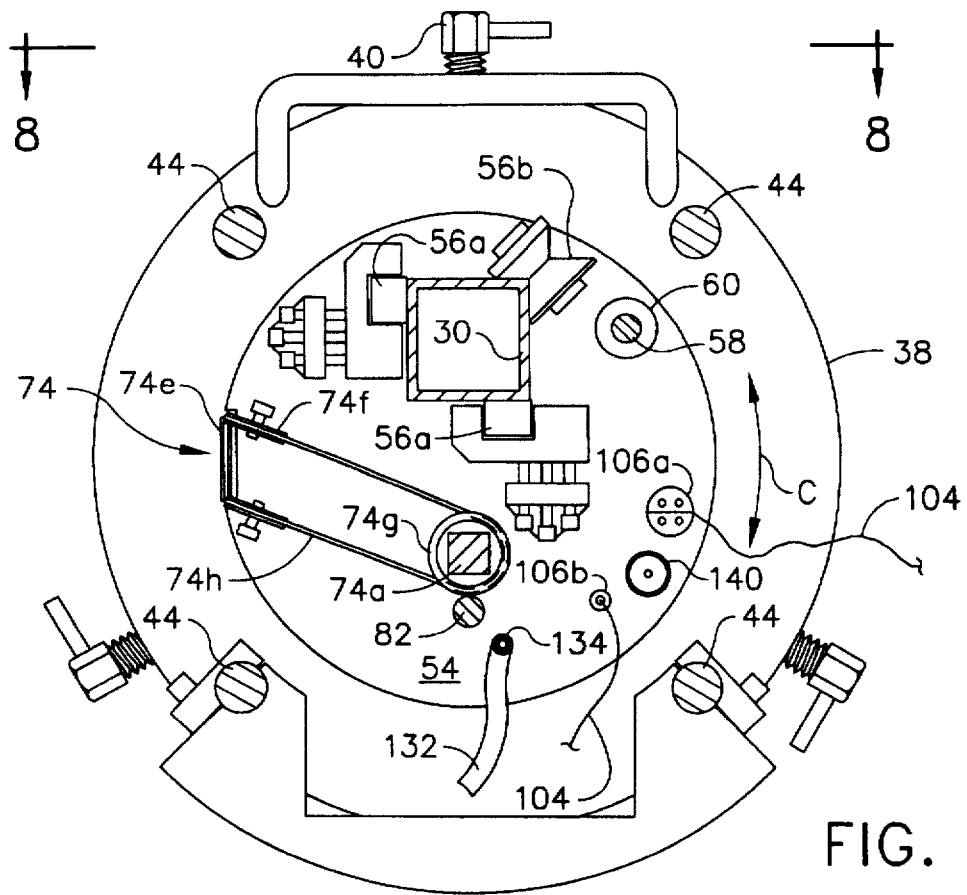
FIG. 7 is a partly sectional, elevational, forward-facing-aft view of a carriage assembly illustrated in FIG. 2 and taken along line 7—7.
Figure 8:
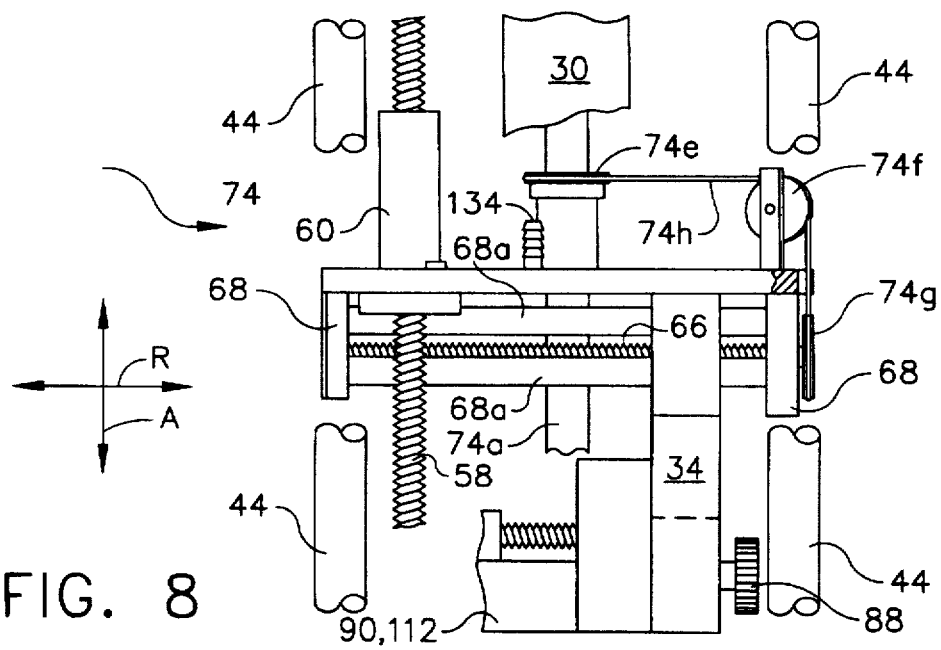
FIG. 8 is a partly sectional top view of the carriage assembly illustrated in FIG. 7 and taken along line 8—8.
Figure 9:
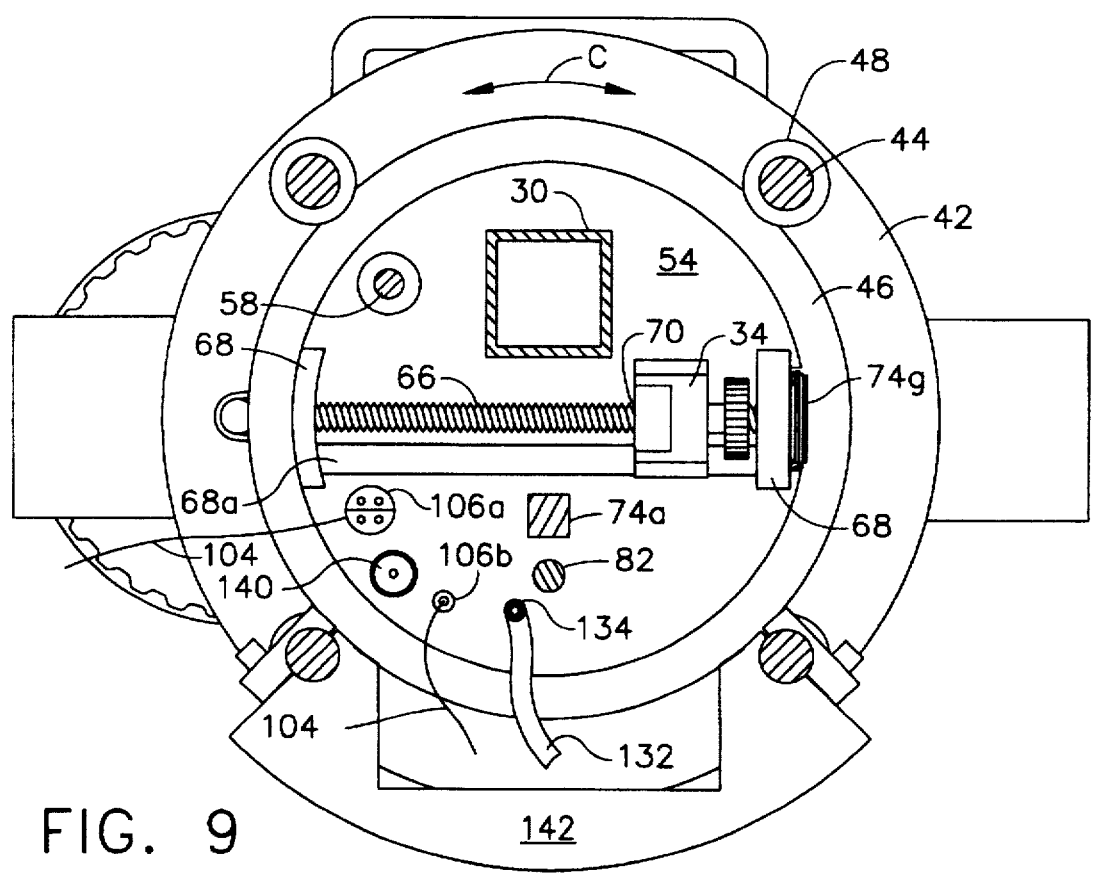
FIG. 9 is a partly sectional, elevational, aft-facing-forward view of the carriage assembly illustrated in FIG. 2 and taken along line 9—9.

The carriage assembly 32 illustrated in FIG. 2 is shown in more detail in conjunction with FIGS. 7–9 and includes an annular scanner or carriage plate 54 suitably mounted on the support beam 30 for axial movement (A) therealong, and circumferential rotational movement (C) therewith. As shown in FIG. 7, since a single support beam 30 is being used, it preferably has a square tube configuration for structural rigidity and effecting circumferential rotation of the carriage assembly 32. And, two spring loaded wheels 56a and a V-shaped corner wheel 56b are used to mount the carriage plate 54 for solely rolling axial movement on the support beam 30.

Also shown in these FIGS. 2 and 7–9 is an axial-drive (AD) lead screw or ball screw 58 extending axially from the CD plate 46 to the aft support assembly 28 (see also FIG. 1). The drive assembly 26 also includes a cooperating axial ball screw nut 60, shown best in FIGS. 2 and 8, which is fixedly joined to the forward face of the carriage plate 54, and threadingly receives therethrough the AD screw 58. An axial-drive (AD) motor 62 is fixedly joined to the forward surface of the CD plate 46, and a corresponding axial-drive (AD) transmission 64 as shown in FIGS. 2 and 6 is suitably joined between the AD motor 62 and the AD spool 58 for rotating the AD spool 58 to axially translate (A) the carriage plate 54 along the support beam 30. In this way, the AD motor 62 which is joined to the rotatable CD plate 46 can axially translate the carriage plate 54, with rotation of the CD plate 46 rotating the carriage plate 54 via the interjoined support beam 30 for effecting two-axis (C and A) movement of the carriage plate 54.

Since the probe support 34 is carried on the carriage plate 54, it also has these two axes of movement. In order to effect the third axis of movement of the probe support 34, the drive assembly 26 further includes a radial-drive (RD) lead screw or ball screw 66 shown in FIGS. 8 and 9 which is suitably joined to the aft surface of the carriage plate 54 generally radially thereon. The RD screw 66 as illustrated in FIG. 9 is suitably mounted in respective bearings in opposite end plates 68 which in turn are fixedly joined to the carriage plate 54. The probe support 34 includes a screw hole 70 having internal threads which threadingly receives the RD screw 66. Extending between the end plates 68 and passing through complementary apertures in the probe support 34 are a pair of spaced apart guide rods 68a as illustrated in FIGS. 8 and 9 which ensure even radial translation of the probe support 34 as the RD screw 66 rotates for correspondingly translating the probe support 34 therealong.

As shown in FIG. 2, a radial-drive (RD) motor 72 is suitably fixedly joined to the forward surface of the CD plate 46 for rotation therewith, and a suitable radial-drive (RD) transmission 74 as shown in FIGS. 2 and 6–7 is joined between the RD motor 72 and the RD screw 66 to radially translate the probe support 34 along the RD screw 66 on the carriage plate 54. In this way, the probe support 34 can move radially (R) along the RD screw 66, with the carriage plate 54 being movable both axially (A) and with circumferential rotation (C) so that the probe support 34, and in turn the probe mounted thereto, have three-axis movement for inspecting the various surfaces of the compressor spool rotor disks 16.

Figure 10:
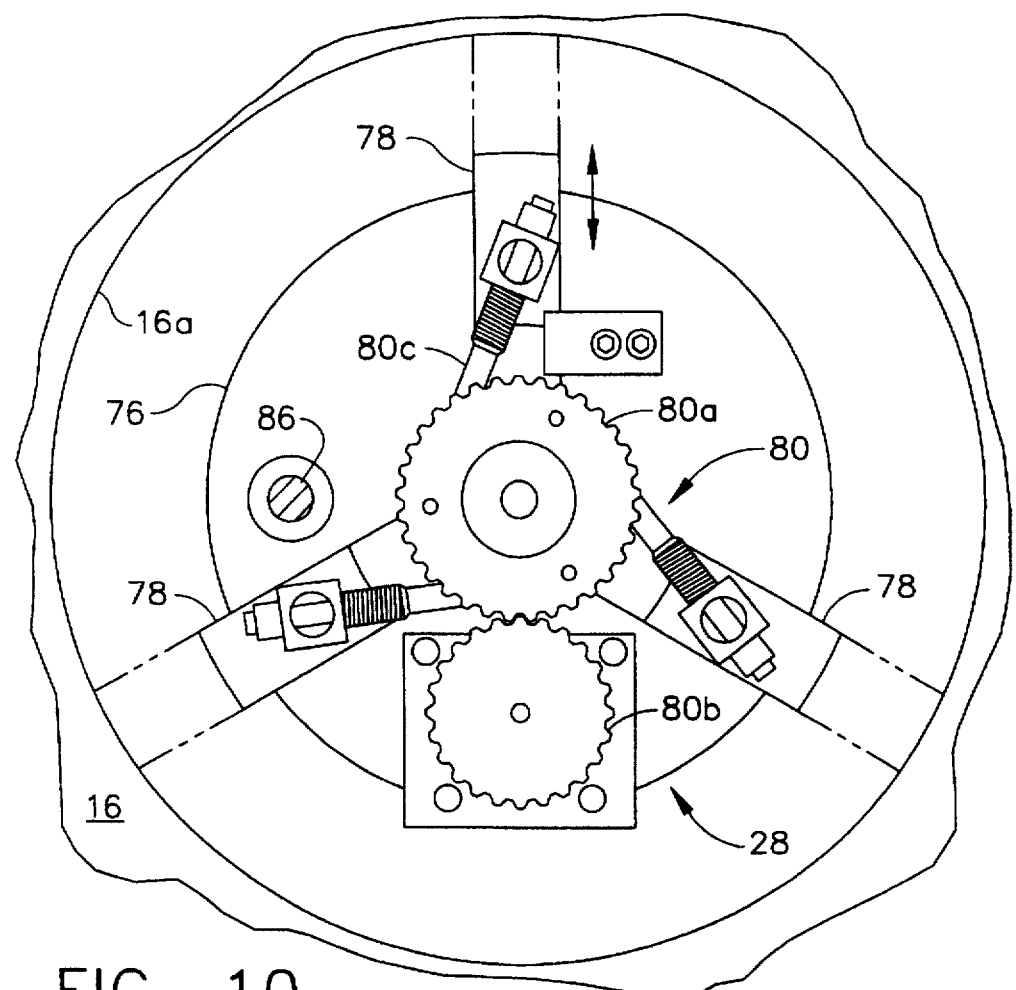
FIG. 10 is an aft-facing-forward end view of the aft support assembly illustrated in FIG. 4 and taken along line 10—10.

The aft support assembly 28 is illustrated in more particularity in FIGS. 4 and 10 and is generally joined by the support beam 30 to the CD plate 46. The aft support assembly 28 includes an annular support plate 76 which is rotatably mounted to the distal end of the support beam 30 for allowing circumferential rotation (C) of the support beam 30 relative thereto. Three circumferentially spaced apart locking arms 78 are suitably radially slidably joined to the aft face of the support plate 76. A suitable locking transmission 80 for actuating the locking arm 78 is joined between the support plate 76 and the three locking arms 78 for radially retracting and extending the locking arms 78 as shown in solid and phantom lines in FIG. 10. A corresponding locking shaft 82 extends axially from the CD plate 46 of the drive assembly 26 as illustrated in FIG. 2 to the locking transmission 80 illustrated in FIG. 4, and is selectively engagable therewith for radially positioning the locking arms 78 to fixedly abut an inner bore 16a of the aft-most (stage ten) disk 16 of the compressor spool 12 for fixedly joining the aft support assembly 28 thereto without movement relative thereto when engaged or locked. Each of the locking arms 78 is generally L shaped and preferably includes an integral rubber pad at its top end which is radially positionable in compression contact with the disk inner bore 16a.

The locking transmission 80 as shown in FIGS. 4 and 10 includes a pair of mating gears 80a,b, with the second gear 80b being selectively, manually driven by the locking shaft 82 when required. From the back side of the first gear 80a extend three spring loaded drive arms 80c pivotally joined to respective ones of the locking arms 78. Upon rotation of the second gear 80b, the first gear 80a rotates, to in turn translate the drive arms 80c, which in turn extend or retract the locking arms 78.

As shown in FIG. 4, the aft support assembly 28 further includes an annular idler plate 84 suitably rotatably joined coaxially with the support plate 76 for free or unrestrained circumferential rotation relative thereto. A center shaft joins the support and idler plates 76, 84 with suitable bearings being used. In this way, the idler plate 34 may rotate freely circumferentially (C) while the support plate 76 is fixedly joined to the stationary rotor disk 16 and therefore does not rotate or otherwise move. The support beam 30 and the AD screw 58 are suitably fixedly and rotatably, respectively, joined to the forward face of the idler plate 34 for circumferential rotation (C) therewith to allow the carriage plate 54 (see FIG. 2) to rotate upon actuation of the CD motor 50.

The locking shaft 82 shown in FIGS. 1,2, and 4 extends axially slidably through a respective aperture in the idler plate 84 and is selectively engagable with the second gear 80b of the locking transmission 80 joined to the support plate 76 for suitably actuating the locking arms. 78. As shown in FIG. 2, the forward end of the locking shaft 82 has a hand wheel, and the aft end of the locking shaft 82 as illustrated in FIGS. 4 and 10 is preferably square for selectively engaging a respective square hole at the center of the second gear 80b of the locking transmission 80 when desired to extend or withdraw the locking arms 78.

Also shown in FIG. 4 is an optional elongate guide rod 86 having a bulbous guide or handle at one end and suitable screw threads at the other end. During initial installation of the scanner 10 through the compressor spool 12, the guide rod 86 may be inserted through a respective access hole in the support plate 76 and is threadingly engaged in a mating aperture in the idler plate 84 upon initial manual alignment thereof effected by turning the manual hand wheel of the CD motor 50. The guide rod 86 would be initially inserted through either the aft end of the compressor spool 12 or through the center opening of both the HPT module 14c and the LPT module 14d to engage the scanner aft supporting assembly 28 inserted from the forward end of the compressor spool 12. In this way, maintenance workers may be used at both ends of the engine 14 for initially inserting the scanner 10 using the guide rod 86, which would then be removed for allowing rotation of the idler plate 84 relative to the locked and stationary support plate 76.

FIGS. 2 and 5 illustrate in more particularity the details of the exemplary CD transmission 52. It includes a drive shaft 52a fixedly joined at a proximal end thereof to the center of the CD plate 46, and has a bull or large pulley 52b at the free distal end thereof. A pinion or small pulley 52c is fixedly joined to the output shaft of the CD motor 50 as illustrated in FIG. 5. A first idler pulley 52d is fixedly joined to one end of an idler shaft 52e, and a second idler pulley 52f, smaller than the first pulley 52d, is fixedly joined to the opposite end of the idler shaft 52e. Respective drive belts 52g and 52h are joined to the pinion pulley 52c and the first idler pulley 52d, and between the second idler pulley 52f and the bull pulley 52b. In this way, the variously sized pulleys provide increasing torque for circumferentially rotating (C) the drive shaft 52a and in turn the CD plate 46 upon rotation of the CD motor 50 in either of two opposite directions.

The AD transmission 64 is illustrated in more particularity in FIG. 6 and includes a first pulley 64a fixedly joined to the forward end of the AD screw 58. A second pulley 64b is fixedly joined to the output shaft of the AD motor 62. And, a drive belt 64c joins the first and second pulleys 64a,b for rotating the AD screw 58 upon rotation of the AD motor 62 in either of opposite directions. The AD motor 62 has an optional hand wheel for manually turning its output shaft if desired.

The RD transmission 74 is illustrated in more particularity in FIGS. 2, 4, and 6–9 and includes a preferably square drive shaft 74a extending axially from the CD plate 46 to the idler plate 84 to which it is suitably rotatably mounted in a suitable bearing or bushing. A first pulley 74b is fixedly joined to the output shaft of the RD motor 72 (see FIG. 6). A second pulley 74c is fixedly joined to the forward end of the RD drive shaft 74a adjacent to the CD plate 46 (see FIG. 6). A first drive belt 74d joins the first and second pulleys 74b,c to rotate the RD drive shaft 74a upon rotation of the RD motor 72 in either of two opposite directions. The RD motor 72 has an optional hand wheel for manually turning its output shaft if desired.

As shown in FIG. 8, a third pulley 74e is suitably rotatable mounted to the forward face of the carriage plate 54 by a suitable bearing and is axially slidably mounted around the RD drive shaft 74a for rotation therewith. Since the RD drive shaft 74a is preferably square, the third pulley 74e may simply have a complementary square aperture therethrough and is rotatable driven by the drive shaft 74a while permitting relative axial movement therebetween. A pair of idler pulleys 74f (see also FIG. 7) are rotatably mounted to the forward side of the carriage plate 54. A fourth pulley 74g is fixedly joined to one end of the RD screw 66 on an opposite, aft side of the carriage plate 54. A second drive belt 74h joins the third and fourth pulleys 74e and 74g via the idler pulleys 74f to rotate the RD screw 66 upon rotation of the RD drive shaft 74a in either of two opposite directions. The third and fourth pulleys 74e,d are disposed perpendicularly to each other in this exemplary embodiment, and the idler pulleys 74f are disposed therebetween in a general triangular configuration for transferring the rotation of the drive shaft 74a into corresponding rotation of the RD screw 66 disposed perpendicularly thereto.

The various drive belts and pulleys disclosed above may either be smooth or cogged as desired for obtaining accuracy of movement in the three axes A, C, and R. All three transmissions 52, 64, and 74 utilize relatively simple pulleys and belts for providing the relatively sophisticated three-axis movement of the probe support 34 between the drive assembly 26 and the aft support assembly 28 for accessing various inspection surfaces of the several rotor disks 16 of the compressor spool 12.

The scanner 10 described above and illustrated in FIGS. 2 and 4 for example, is readily manually portable for being suitably positioned into the compressor spool 12. It may then be configured for conducting various operations including cleaning and inspection of various surfaces inside the compressor spool 12. Any type of device may be attached to the three-axis probe support 34 using a simple hand screw 88 as shown in FIG. 8 which passes through an aperture in the probe support 34 itself and is threaded at its distal end for threadingly engaging the base of the desired attachment.

Figure 11:
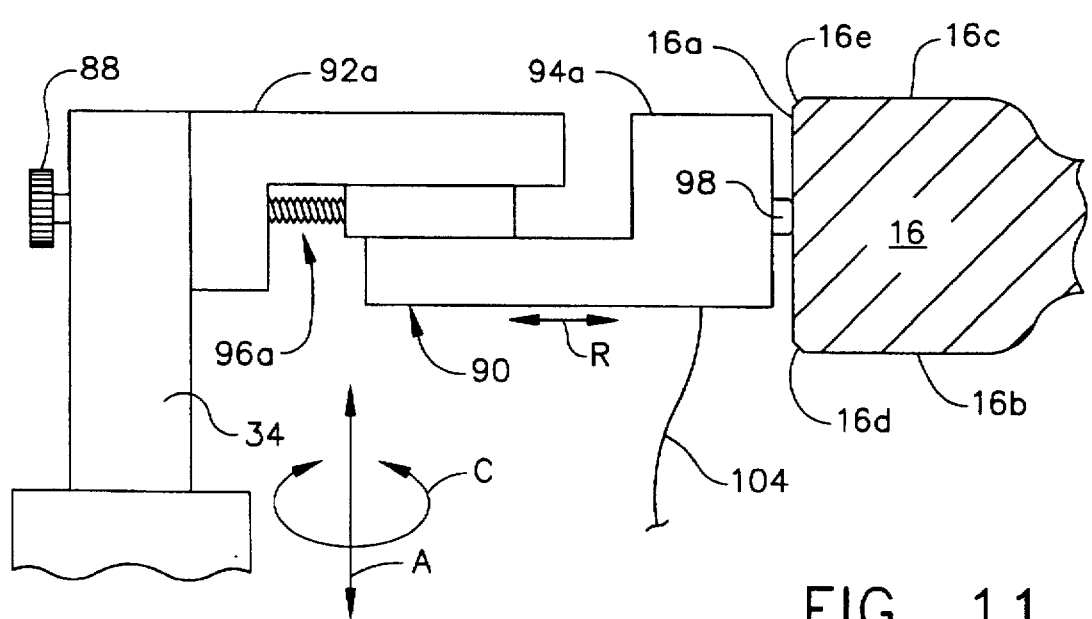
FIG. 11 is a side view of a first embodiment of an eddy current probe mounted to a probe support on the carriage assembly illustrated in FIG. 2 for inspecting a bore of a rotor disk of the compressor spool.

FIG. 11 illustrates an exemplary scanner probe in the form of an eddy current probe 90 which is removably mounted to the probe support 34 using the hand screw 88 and is selectively positionable axially (A), circumferentially (C), and radially (R) inside the compressor spool 12 at a desired rotor disk 16 for conventional eddy current inspection thereof. As shown in FIG. 11, the exemplary rotor disk 16 includes the inner bore 16a and forward and aft faces 16b, 16c adjacent thereto, and transitioning forward and aft chamfers 16d and 16e therebetween. Various embodiments of the probe 90 may be configured and positioned on the probe support 34 to inspect each of the disk inner bore 16a, forward and aft faces 16b, 16c, and the forward and aft chamfers 16d, 16e.

The exemplary probe 90 illustrated in FIG. 11 includes a base portion or arm 92a which is removably fixedly joinable to the probe support 34 by threading the hand screw 88 through the probe support 34 into the base support 92a. The probe 90 further includes a tip arm or portion 94a which is suitably compressible joined to the base portion 92a by a conventional spring and slide assembly 96a for providing relative translation therewith. A conventional eddy current probe sensor 98 is suitably mounted to the distal end of the tip portion 94a. The sensor 98 is a conventional electrical coil for generating an AC magnetic field which is used for conventionally inspecting the rotor disk 16 of the spool 12 by conventional eddy current inspection.

In the exemplary embodiment illustrated in FIG. 11, the spring and slide assembly 96a join the tip portion 94a and the base portion 92a for solely relative radial translation therebetween so that the sensor 98 may be radially positioned in abutment against the bore 16a of a respective spool disk 16. The probe support 34 is moved initially to position the sensor 98 at the desired axial position (A) under one of the rotor disks 16. The probe support 34 is then circumferentially rotated to position the sensor 98 at the desired rotational position (C) along the inner bore 16a. And then, the probe support 34 is moved radially outwardly (R) until the sensor 98 abuts the desired inspection site, with the spring and slide assembly 96a relieving excessive compressive force on the sensor 98 for preventing damage thereto.

The eddy current sensor 98 itself is conventional and is suitably electrically joined to a conventional eddy current instrument 100 illustrated in FIG. 1 which in turn is suitably connected to a conventional strip chart recorder 102 for example. To allow easy interchangeability of the various attachments to the probe support 34, a variety of suitable quick connectors are preferably installed on the carriage plate 54 as illustrated in FIGS. 7 and 9 for example. In FIG. 11, a suitable electrical sensor cable 104 is routed from the eddy current sensor 98 to a conventional quick connector 106a mounted on the aft side of the carriage plate 54 as illustrated in FIG. 9. An identical quick connector 106a is also mounted on the opposite forward side of the carriage plate 54 as illustrated in FIG. 7, with an extension of the sensor cable 104 being joined thereto and then further routed to the eddy current instrument 100 as illustrated in FIG. 2. A conventional electrical controller 108, which is preferably a programmable computer, is suitably joined to a conventional controller connection 108a which in turn is suitably connected by a cable bundle to a junction box 108b which in turn is suitably electrically connected to the three drive motors 50, 62, and 72. The controller 108 controls all operations of the scanner 10. In this way, the specific attachment to the probe support 34 may be accurately positioned inside the spool 12, and the eddy current probe 90, for example, may be used for conducting conventional eddy current inspection at the desired location.

Figure 12:
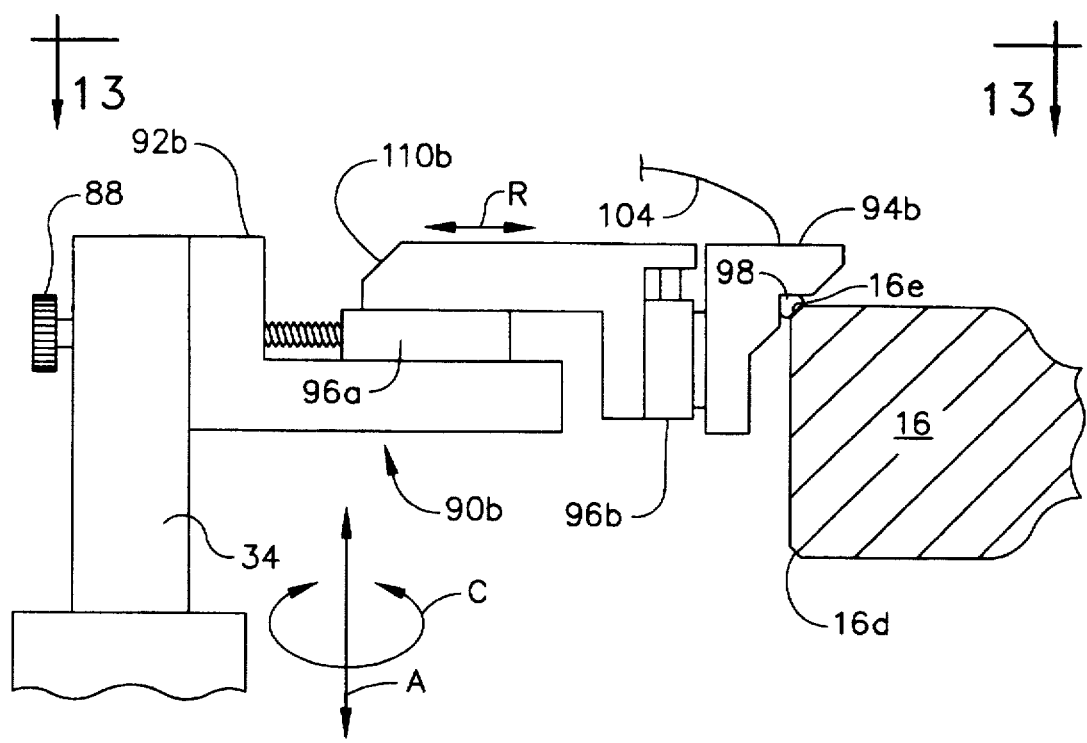
FIG. 12 is a side view of a second embodiment of an eddy current probe joined to the probe support in FIG. 2 for inspecting a chamfer of the compressor spool disk.
Figure 13:
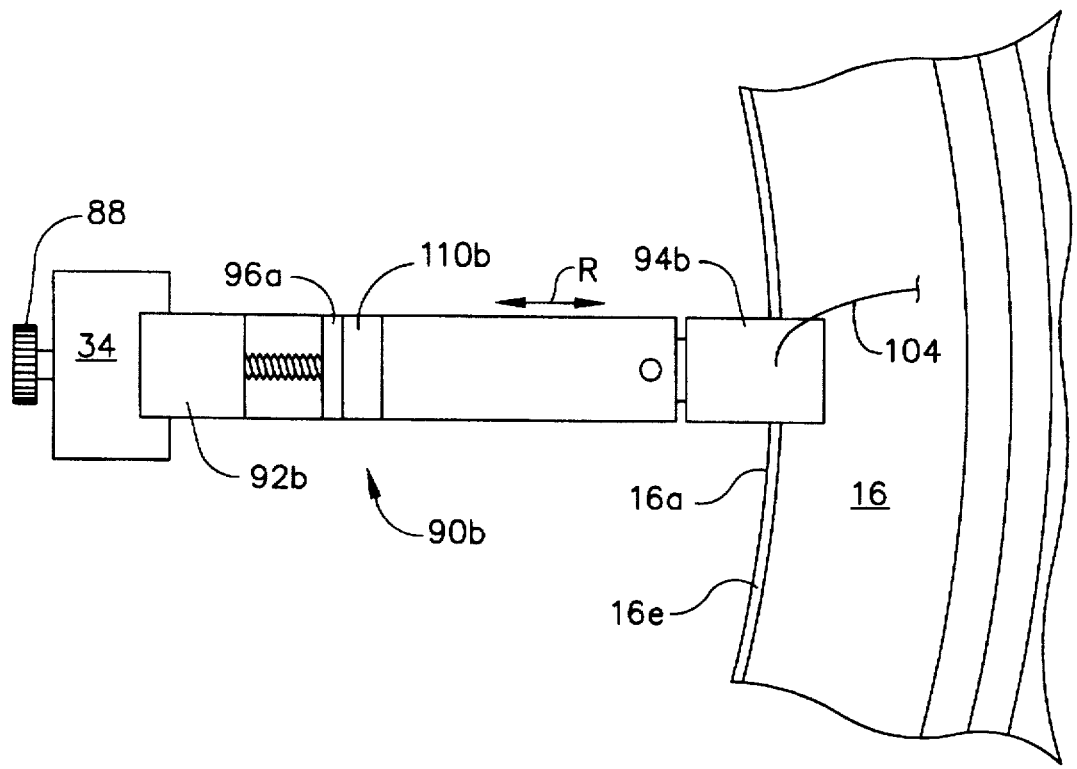
FIG. 13 is an end view of the eddy current probe illustrated in FIG. 12 and taken along line 13—13.

The probe 90 illustrated in FIG. 11 is specific for inspecting the inner bores 16a. FIGS. 12 and 13 illustrate another embodiment of the eddy current probe 90b which similarly includes a base portion 92b removably joined to the probe support 34, and a tip portion 94b which suitably configured for supporting the eddy current sensor 98. In this configuration, the tip portion 94b is configured for positioning the sensor 98 perpendicularly to the inclined aft chamfer 16e, and therefore the surrounding area of the sensor 98 is preferably flat and inclined at about 45° to the centerline axis of the engine 22. The probe 90b therefore preferably includes an intermediate portion 110b which is compressibly joined to the base portion 92b by a spring and slide assembly 96a for allowing relative radial movement therewith. The intermediate portion 110b is compressibly joined to the tip portion 94b by a similar spring and slide assembly 96b which allows relative axial movement therebetween. This arrangement allows the sensor 98 to undergo both radial and axial translation relative to the base portion 92b so that the sensor 98 may be radially and axially positioned in abutment against the aft chamfer 16e. A portion of the disk 16 is illustrated in phantom in FIG. 12 to represent the initial radially outward movement of the probe 90b which simultaneously compresses the spring and slide assemblies 96a,b as the tip portion 94b contacts the disk 16. In this way, the sensor 98 may be accurately positioned in abutment against the aft chamfer 16e without undesirable compression loads being generated. For correspondingly inspecting the forward chamfer 16d, the probe 90b may simply be axially inverted so that probe 98 may be positioned perpendicularly against the forward chamfer 16d.

Figure 14:
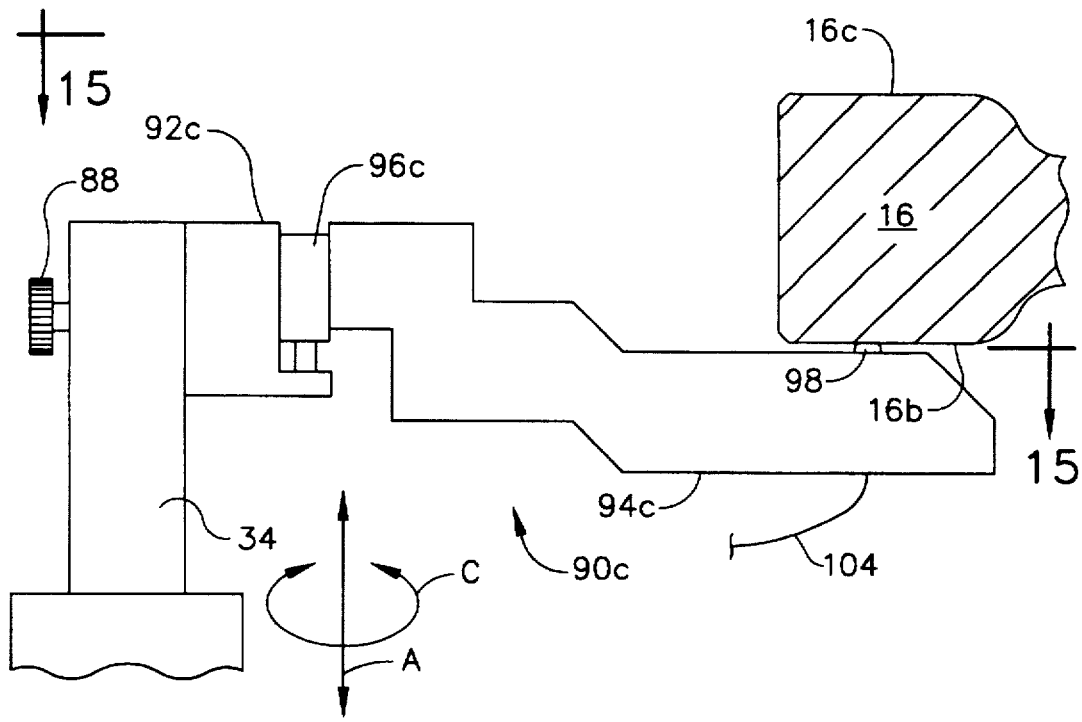
FIG. 14 is a side view of a third embodiment of an eddy current probe joined to the probe support illustrated in FIG. 2 for inspecting a side surface of the compressor rotor disk.
Figure 15:
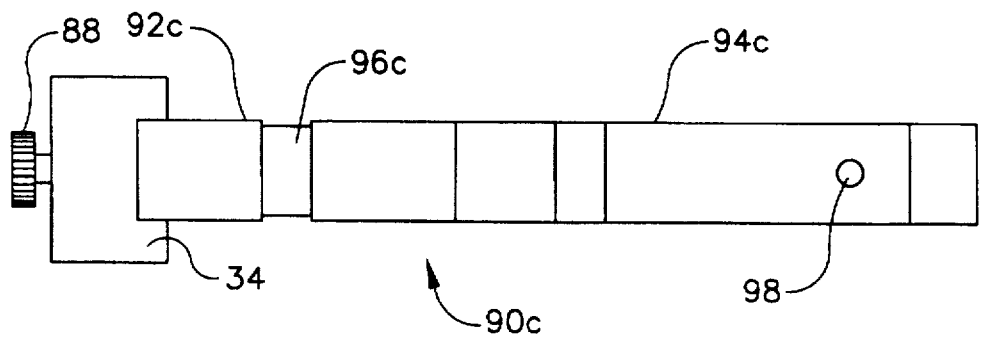
FIG. 15 is an end view of the eddy current probe illustrated in FIG. 14 and taken along line 15—15.

Illustrated in FIGS. 14 and 15 is yet another embodiment of the eddy current probe 90c where again the base portion 92c is removably joined to the probe support 34, with the tip portion 94c being configured for positioning the sensor 98 for inspection of the forward face 16b of the disk 16. In this embodiment, the spring and slide assembly 96c compressibly joins the tip portion 94c to the base portion 92c for relatively axial translation therebetween so that the sensor 98 may be axially positioned in abutment against the disk forward face 16b. In this embodiment, the sensor 98 may be radially and circumferentially initially positioned adjacent to the disk forward face 16b and then as the sensor 98 is axially translated aft against the forward face 16b, the spring and slide assembly 96c correspondingly compresses to firmly position the sensor 98 against the forward surface 16b without damaging the sensor 98. Again, the probe 90c illustrated in FIG. 14 may be simply axially inverted for inspecting the aft face 16c in a manner similar to the inspection of the forward face 16b.

Figure 16:
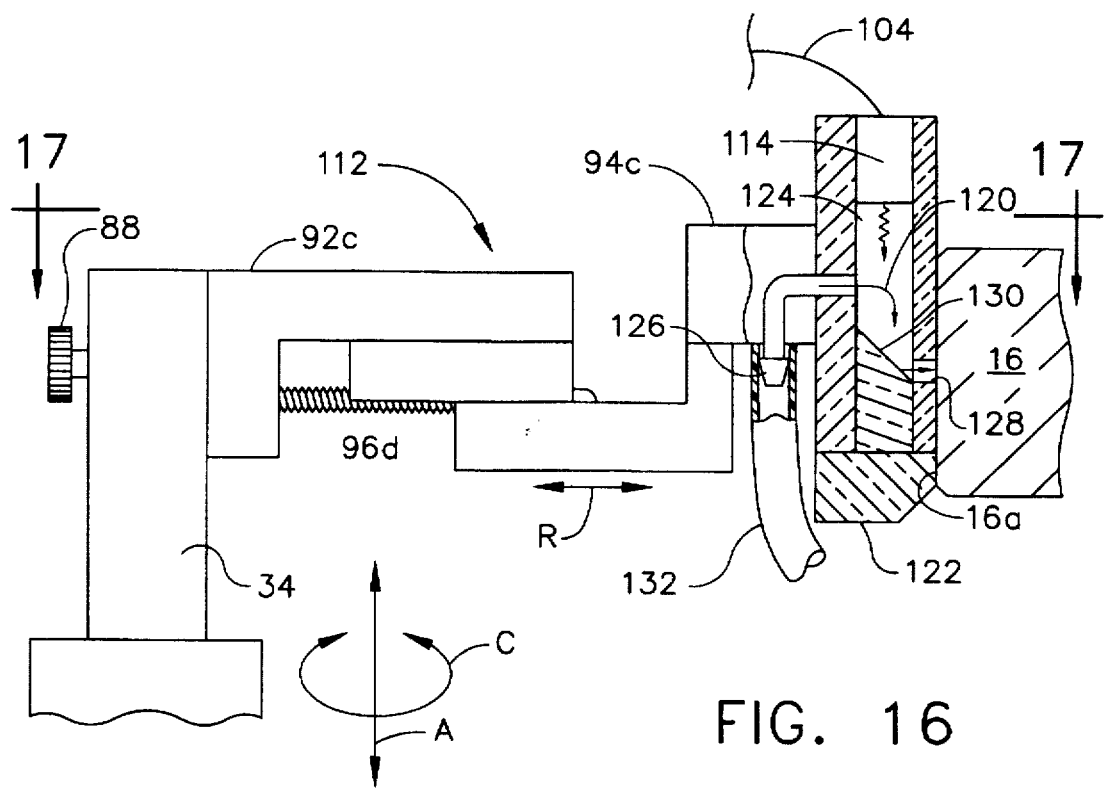
FIG. 16 is a side view of a first embodiment of an ultrasonic probe mounted to the probe support illustrated in FIG. 2 for inspecting the bore of the compressor spool disk.
Figure 17:
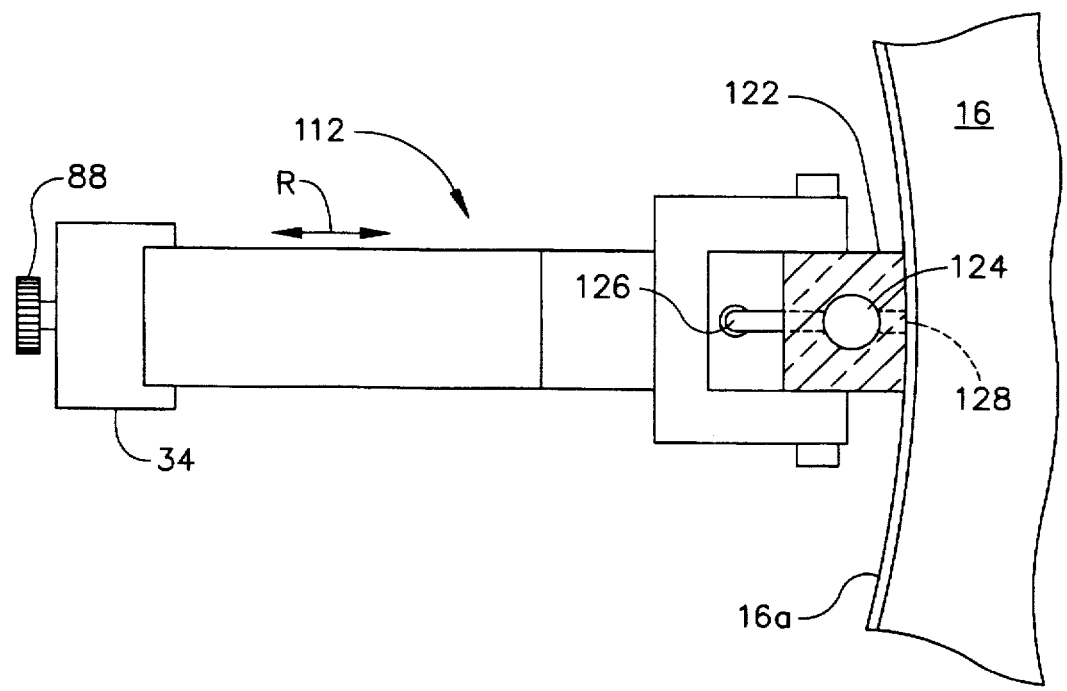
FIG. 17 is an end view of the ultrasonic probe illustrated in FIG. 16 and taken along line 17—17.

Illustrated in FIGS. 16 and 17 is an exemplary embodiment of an ultrasonic probe 112 which is also removably mounted to the probe support 34 and is similarly selectively positionable axially, circumferentially, and radially inside the desired disk 16 of the spool 12 for ultrasonic inspection thereof. The ultrasonic probe 112 similarly includes a base portion 92c removably fixedly joined to the probe support 34 by the hand screw 88, and the corresponding tip portion 94c is compressibly joined to the base portion 92c by a suitable spring and slide assembly 96d for relative radial translation therebetween so that a conventional ultrasonic transducer or sensor 114 may be suitably positioned for ultrasonic inspection of the disk inner bore 16a. In this embodiment, the sensor 114 is electrically joined by a dedicated cable 104 suitably configured for this purpose which in turn is provided with a respective conventional quick connection 106b on the aft side of the carriage plate 54 as illustrated in FIG. 9, with a similar quick connection 106b being provided on the forward side of the carriage plate 54 as illustrated in FIG. 7. The cable 104 is preferably a bundle containing dedicated conductor wires for both the eddy current sensor 98 and the ultrasonic sensor 114 which are connected as required. The cable 104 is then routed to a conventional ultrasonic instrument 116 as illustrated in FIG. 2. A conventional strip chart recorded 118 is operatively joined to the instrument 116. In this way, the ultrasonic sensor 114 may be used in a conventionally known manner for conducting ultrasonic inspection of the compressor spool 12.

However, conventional ultrasonic inspection requires a coupling fluid such as water between the ultrasonic transducer and the inspection site, and is typically conducted completely under water. In order to maintain portability of the scanner 10 in accordance with one desired objective of the present invention, suitable means are illustrated in FIGS. 2, 16 and 17 for channeling a coupling fluid such as water 120 to the inspection site for coupling the ultrasonic transducer 114 to the disk 16. As shown in FIGS. 16 and 17, a bubbler housing 122 which may be formed of a suitable plastic such as plexiglass is suitably attached to the probe tip portion 94c. The housing 122 includes an inner channel 124 in which is mounted the ultrasonic sensor 114. A fluid inlet 126 extends through the housing 122 for channeling the fluid 120 into the channel 124. The channel 124 has an outlet aperture 128 and a suitable reflective surface or mirror 130 upstream thereof. In this way, ultrasonic waves may be passed through the channel 124 filled with the fluid 120 and bounce off the mirror 130 and through the outlet 128 against the disk 16 for ultrasonic inspection thereof.

The housing 122 is resiliently compressed against the disk bore 16a and provides an effective contact seal around the outlets 128. The coupling fluid 120 is provided to the inlet 26 by a suitable flexible tube 132 which is routed to the aft side of the carriage plate 54 as illustrated in FIG. 9 and is removably joined thereto by a conventional quick connect fluid fitting 134. The forward side of the carriage plate 54 as illustrated in FIG. 7 similarly includes an identical fitting 134, with the tube 132 continuing its routing from the carriage plate 54 to a conventional pump 136 which in turn is joined to a conventional water supply 138. The pump 136 is suitably connected to the controller 108. Accordingly, in operation, the pump 136 is controlled for channeling the coupling fluid 120 through the tube 132 to the bubbler housing 122 wherein it provides suitable ultrasonic coupling for the ultrasonic waves generated by the transducer 114 for inspecting the disk 16.

Figure 18:
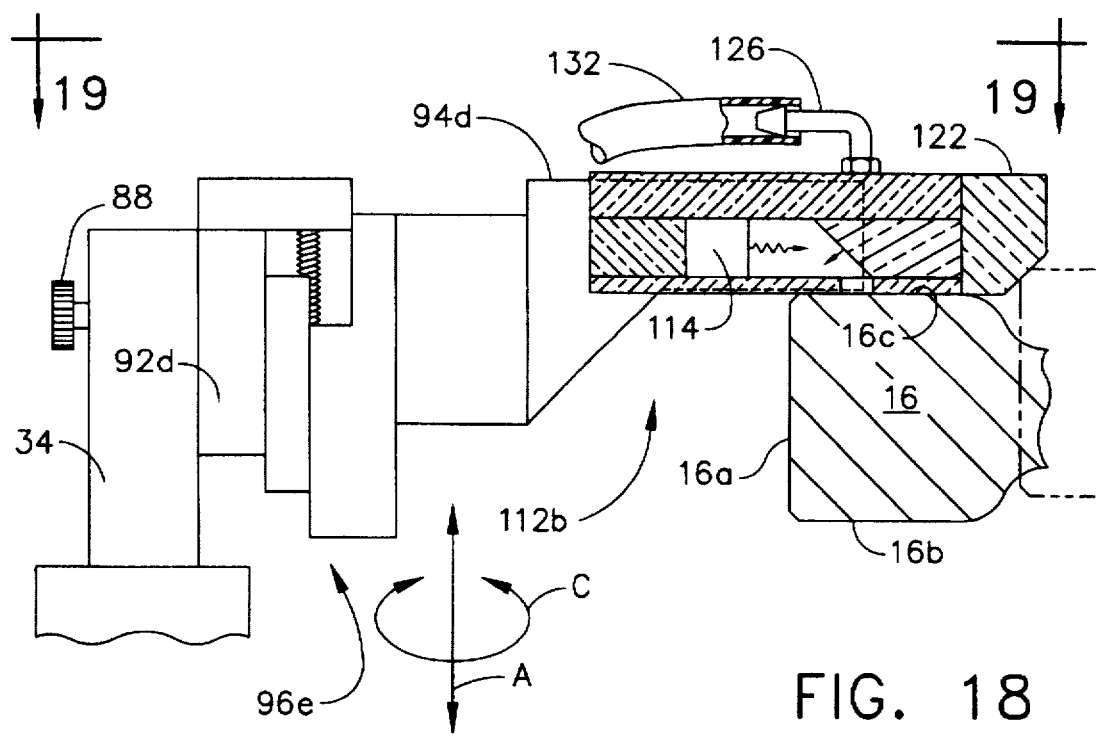
FIG. 18 is a side view of a second embodiment of an ultrasonic probe joined to the probe support illustrated in FIG. 2 for inspecting the side surface of the compressor spool disk.
Figure 19:
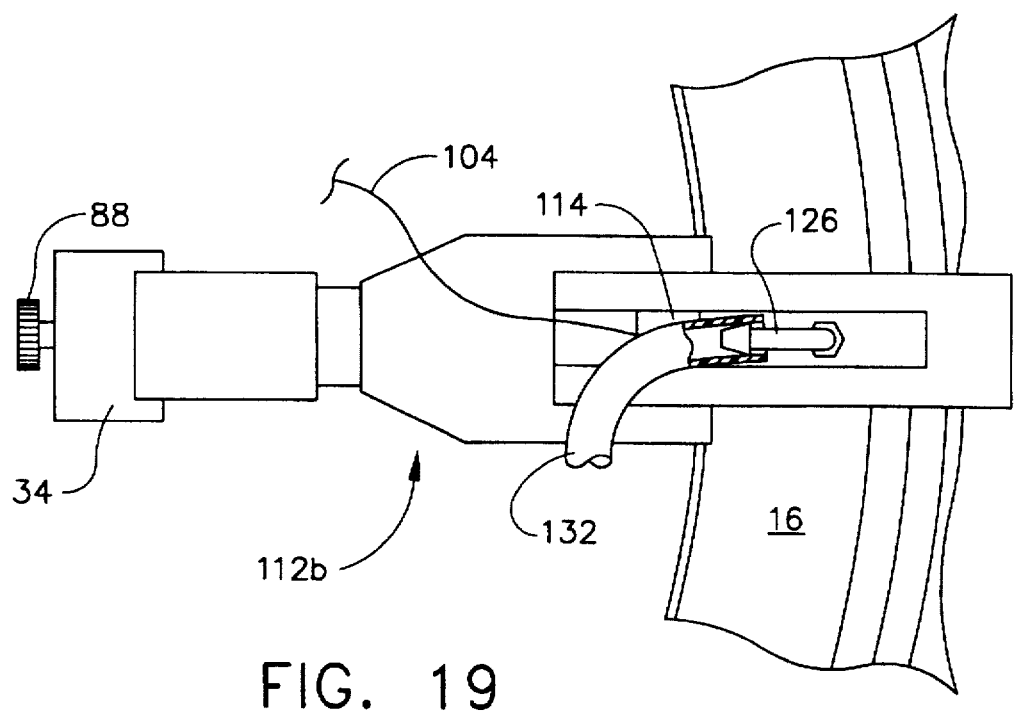
FIG. 19 is an end view of the ultrasonic probe illustrated in FIG. 18 and taken along line 19—19.

FIGS. 18 and 19 illustrate another embodiment of the ultrasonic probe 112b configured for conducting ultrasonic inspection of the disk aft face 16c. In this embodiment, the tip portion 94d is configured for positioning the bubbler housing 122 parallel to the disk aft face 16c and is compressibly joined to the base portion 92d by a suitable spring and slide assembly 96e for allowing relative axial translation therebetween so that the bubbler housing 122 may be positioned axially in abutment against the disk aft face 16c. For correspondingly inspecting the disk forward face 16b, the probe 112b may be simply axially inverted on the probe support 34.

Although various embodiments of eddy current probes 90 and ultrasonic probes 112 have been described above, these probes may take various other configurations as desired since they may be simply attached and removed from the three-axis probe support 34. The quick connections on the carriage plate 54 allow for easy assembly and disassembly of the required electrical or fluid connections as indicated above. The carriage plate 54 may have other quick connections as desired such as a quick connection 140 as illustrated in FIGS. 7 and 9 for one or more conventional proximity sensors which may also be used in the scanner 10. Proximity sensors are conventional and are used for allowing the probe support 34 to be returned to a home position before accurate placement of the probe support 34 is made.

The scanner 10 as shown in FIGS. 2 and 9 may also include a suitable calibration standard or block 142 specifically configured to match the contour of the inspection site such as the disk bores 16a, with the block 142 having a predetermined defect therein such as a drilled hole. In this way, before testing of the disk, the appropriate eddy current probe 90 or ultrasonic probe 112 may be initially positioned adjacent to the calibration block 142 to calibrate the instrumentation.

The probe support may be used for other purposes such as the attachment of a suitable cleaning arm (not shown) which may be used for cleaning the inspection surfaces inside the spool 12 as required in conjunction with the inspection process.

Upon completion of the inspection process, the probe support 34 and the probe attached thereto are returned to the home position within the drive assembly 26. The support plate 76 and the idler plate 84 illustrated in FIG. 4 are suitably circumferentially aligned so that the locking shaft 82 may be engaged with the locking transmission 80 for disengaging the locking arms 78 from the disk 16. The optional guide rod 86 may be engaged with the idler plate 84 if desired for assisting in removing the entire scanner 10 axially forwardly from the spool 12. The collar 36 may then be removed from the spool 12, with the fan module 14a then being reinstalled at the forward end of the compressor module 14b.

Accordingly, the disk 16 of the compressor spool 12 may be both inspected using conventional eddy current coils and ultrasonic transducers in situ without requiring disassembly of the entire compressor module 14d. This significantly decreases the time required for inspection and of course saves substantial cost.

While there have been described herein what are considered to be preferred and exemplary embodiments of the present invention, other modifications of the invention shall be apparent to those skilled in the art from the teachings herein, and it is, therefore, desired to be secured in the appended claims all such modifications as fall within the true spirit and scope of the invention.

Accordingly, what is desired to be secured by Letters Patent of the United States is the invention as defined and differentiated in the following claims:

We claim:

1. A scanner for inspecting the inside of a spool comprising:

a forward drive assembly being fixedly mountable to a forward end of said spool;

an aft support assembly being fixedly mountable to an aft end of said spool;

a support beam extending between said drive and support assemblies; and a carriage assembly mounted on said support beam and including a probe support for mounting a removable scanner probe for inspecting said spool;

said drive assembly including means for axially translating said carriage assembly along a longitudinal axis extending from said drive assembly to said support assembly, means for rotating said carriage assembly circumferentially about said longitudinal axis, and means for radially translating said probe support on said carriage assembly so that said probe support has three-axis movement including axial, circumferential, and radial, respectively, for being selectively positioned inside said spool between said forward and aft ends thereof for inspecting said spool.

2. A scanner according to claim 1 wherein said drive assembly comprises:

an annular mounting flange removably mountable to said spool forward end for supporting said drive assembly thereto;

a base plate spaced axially from said mounting flange;

a plurality of frame rods extending axially between said base plate and said mounting flange;

a circumferential-drive (CD) plate mounted to said frame rods for rotation therebetween, with said carriage assembly and said support beam being joined to said CD plate for circumferential rotation therewith;

a CD motor joined to said base plate; and a CD transmission joined between said CD motor and said CD plate for rotating said CD plate circumferentially about said longitudinal axis.

3. A scanner according to claim 2 wherein said carriage assembly comprises a carriage plate mounted on said support beam for axial movement therealong and circumferential rotational movement therewith; and said drive assembly further comprises:

an axial-drive (AD) screw extending axially from said CD plate to said aft support assembly;

an axial ball screw nut fixedly joined to said carriage plate, and threadingly receiving therethrough said AD screw;

an AD motor joined to said CD plate; and an AD transmission joined between said AD motor and said AD screw for rotating said AD screw to axially translate said carriage plate along said support beam.

4. A scanner according to claim 3 wherein said drive assembly further comprises:

a radial-drive (RD) screw joined to said carriage plate generally radially thereon;

said probe support including internal threads receiving said RD screw;

a RD motor joined to said CD plate; and a RD transmission joined between said RD motor and said RD screw to radially translate said probe support along said RD screw on said carriage plate.

5. A scanner according to claim 4 wherein said aft support assembly comprises:

a support plate rotatably mounted to said support beam for allowing rotation of said support beam relative thereto;

a plurality of circumferentially spaced apart locking arms radially slidably joined to said support plate;

a locking transmission joined between said support plate and said locking arms for selectively radially extending and retracting said locking arms; and a locking shaft extending axially from said drive assembly to said locking transmission, and being selectively engagable therewith for radially positioning said locking arm to fixedly abut an inner bore of said spool for fixedly joining said aft support assembly thereto.

6. A scanner according to claim 5 wherein said aft support assembly further comprises:

an idler plate rotatably joined coaxially with said support plate for rotation relative thereto; and said support beam and said AD screw are joined to said idler plate for rotation therewith to allow said carriage plate to rotate upon actuation of said CD motor.

7. A scanner according to claim 6 wherein said locking shaft extends axially slidably through said idler plate and is selectively engagable with said locking transmission joined to said support plate for actuating said locking arms.

8. A scanner according to claim 4 further comprising an ultrasonic probe removably mounted to said probe support and selectively positionable axially, circumferentially, and radially inside said spool for ultrasonic inspection thereof.

9. A scanner according to claim 4 further comprising means for channeling a coupling fluid to said probe or providing ultrasonic coupling between said probe and said spool for ultrasonic inspection thereof.

10. A scanner according to claim 4 further comprising an eddy current probe removably mounted to said probe support and selectively positionable axially, circumferentially, and radially inside said spool for eddy current inspection thereof.

11. A scanner according to claim 4 wherein said spool includes a plurality of axially spaced apart disks each having an inner bore 16a and forward and aft faces, and transitioning forward and aft chamfers therebetween, and said probe is removably mounted to said probe support and is separately configured and positioned to inspect each of said bores, forward and aft faces, and forward and aft chamfers.

12. A scanner according to claim 11 wherein said probe comprises:

a base portion removably fixedly joinable to said probe support;

a tip portion compressibly joined to said base portion for relative translation therewith; and said tip portion includes a sensor for inspecting said spool.

13. A scanner according to claim 12 wherein said tip portion is joined to said base portion for relative radial translation therebetween so that said sensor may be radially positioned in abutment against said spool.

14. A scanner according to claim 12 wherein said tip portion is joined to said base portion for relative axial translation therebetween so that said sensor may be axially positioned in abutment against said spool.

15. A scanner according to claim 14 wherein said tip portion is joined to said base portion for both relative radial and axial translation therebetween so that said sensor may be radially and axially positioned in abutment against said spool.

16. A scanner according to claim 4 wherein said CD transmission comprises:

a CD drive shaft fixedly joined at a proximal end thereof to said CD plate, and having a bull pulley at a distal end thereof;

a pinion pulley fixedly joined to said CD motor;

a first idler pulley fixedly joined to one end of an idler shaft, and a second idler pulley fixedly joined to an opposite end of said idler shaft; and respective drive belts joining said pinion pulley to said first idler pulley, and joining said second idler pulley to said bull pulley for rotating said drive shaft and in turn said CD plate upon rotation of said CD motor.

17. A scanner according to claim 4 wherein said AD transmission comprises:

a first pulley fixedly joined to said AD screw;

a second pulley fixedly joined to said AD motor; and a drive belt joining said first and second pulleys for rotating said AD screw upon rotation of said AD motor.

18. A scanner according to claim 4 wherein said RD transmission comprises:

a drive shaft extending axially from said CD plate to said aft support assembly;

a first pulley fixedly joined to said RD motor;

a second pulley fixedly joined to a forward end of said RD drive shaft adjacent to said CD plate;

a first drive belt joining said first and second pulleys to rotate said RD drive shaft upon rotation of said RD motor;

a third pulley rotatable mounted to said carriage plate and axially slidably mounted around said RD drive shaft for rotation therewith;

a pair of idler pulleys rotatably mounted to one side of said carriage plate;

a fourth pulley fixedly joined to said RD screw on an opposite side of said carriage plate, said third and fourth RD pulleys, being disposed perpendicularly to each other with said RD idler pulleys being disposed therebetween; and a second drive belt joining said third and fourth RD pulleys via said RD idler pulleys to rotate said RD screw upon rotation of said RD drive shaft.

19. A method of inspecting a gas turbine engine spool in situ using said scanner according to claim 1 comprising:

(a) mounting a selected scanner probe to said probe support;

(b) inserting said aft support assembly into said spool from said spool forward end to said spool aft end;

(c) mounting said drive assembly on said spool forward end with said support beam extending axially through said spool;

(d) mounting said aft support assembly to said spool aft end;

(e) operating said drive assembly to selectively position said probe axially, circumferentially, and radially inside said spool adjacent to a selected inspection surface; and (f) operating said probe to inspect said inspection surface.

20. A method according to claim 19 further comprising:

removing a fan module from an assembled gas turbine engine which includes said fan module, a compressor module containing said spool, a high pressure turbine module, and a low pressure turbine module, each of said four modules being removable from each other as complete modules;

installing an adaptor collar to a forward end of said compressor spool; and next effecting said steps (a) through (f), wherein step (c) mounts said drive assembly to said collar.

* * * * *